(12) United States Patent
Sadykhov

(10) Patent No.: US 10,857,311 B2
(45) Date of Patent: Dec. 8, 2020

(54) METHOD AND APPARATUS FOR PRODUCING FINE CONCENTRATED AEROSOL

(71) Applicant: OMEGA LIFE SCIENCE LTD., Migdal Haemek (IL)

(72) Inventor: Akper Sadykhov, Kiryat Mozkin (IL)

(73) Assignee: OMEGA LIFE SCIENCE LTD., Migdal Haemek (IL)

( * ) Notice: Subject to any disclaimer, the term of this patent is extended or adjusted under 35 U.S.C. 154(b) by 718 days.

(21) Appl. No.: 15/467,527

(22) Filed: Mar. 23, 2017

(65) Prior Publication Data

US 2017/0189628 A1 Jul. 6, 2017

Related U.S. Application Data

(63) Continuation-in-part of application No. 13/521,718, filed as application No. PCT/IL2011/000038 on Jan. 12, 2011, now abandoned.
(Continued)

(51) Int. Cl.
*A61M 11/02* (2006.01)
*A61M 15/00* (2006.01)
*A61M 11/00* (2006.01)

(52) U.S. Cl.
CPC .......... *A61M 11/02* (2013.01); *A61M 11/003* (2014.02); *A61M 15/0021* (2014.02);
(Continued)

(58) Field of Classification Search
CPC .... B65D 83/205; B65D 83/38; B65D 25/385; B65D 83/60; A61F 9/0008; B05B 15/008;
(Continued)

(56) References Cited

U.S. PATENT DOCUMENTS 1,023,063 A 4/1912 Bassford
1,132,679 A 3/1915 Murray
(Continued)

FOREIGN PATENT DOCUMENTS

AU 2013292105 A1 1/2015
AU 2013292106 A1 2/2015
(Continued)

OTHER PUBLICATIONS

Atkinson et al., (2009) Natural ventilation for infection control in health-care settings. World Health Organization.
(Continued)

*Primary Examiner* — Tu A Vo
(74) *Attorney, Agent, or Firm* — The Roy Gross Law Firm, LLC; Roy Gross

(57) ABSTRACT

A method and apparatus enabling the production of ultra-fine and concentrated aerosol from liquids, for various applications, by using a rigid porous medium adapted to act as a pneumatic multi-nozzle atomizing system, characterized by having two flat sides and a plurality of pores, and further containing a liquid partially absorbed in the porous medium, thus enabling storage and easy streaming of the aerosol (e.g. for inhalation), fast replacement of liquid carrier device and accuracy of output sprayed dose.

21 Claims, 6 Drawing Sheets

Related U.S. Application Data

Figure 1:
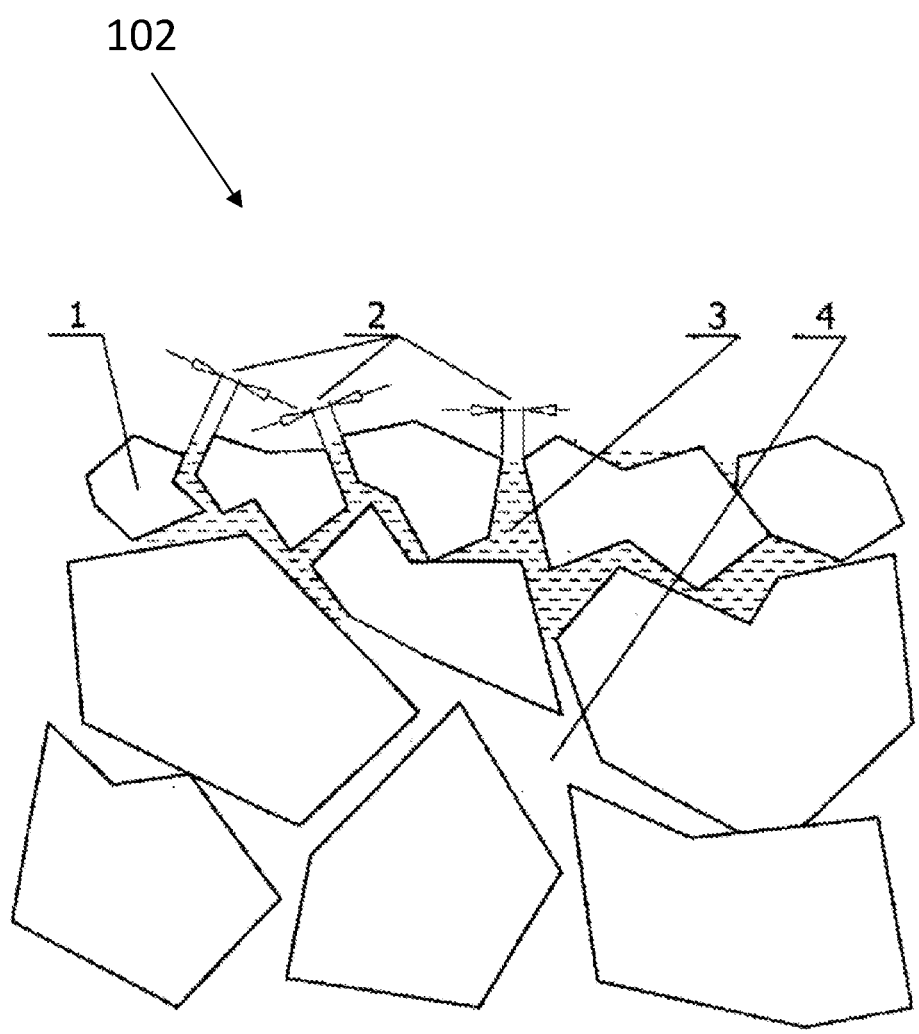

(60) Provisional application No. 61/294,161, filed on Jan. 12, 2010.

(52) U.S. Cl.
CPC .... *A61M 15/0025* (2014.02); *A61M 15/0086* (2013.01); *A61M 2205/073* (2013.01)

(58) Field of Classification Search
CPC . B05B 11/062; B05B 7/0012; G03G 15/0803; A61M 11/00; A61M 11/001; A61M 11/003; A61M 11/006; A61M 11/007; A61M 11/02; A61M 11/04; A61M 15/00; A61M 15/0001; A61M 15/0021; A61M 15/0023; A61M 15/0028; A61M 15/003; A61M 15/0086
See application file for complete search history.

(56) References Cited

U.S. PATENT DOCUMENTS

| | | |
|---|---|---|
| 2,276,878 A | 3/1942 | Rose |
| 2,284,591 A | 5/1942 | Rose |
| 2,348,420 A | 5/1944 | Rose |
| 3,570,038 A | 3/1971 | Jones |
| 3,583,635 A | 6/1971 | Lemelson |
| 3,762,409 A | 10/1973 | Lester |
| 3,812,854 A | 5/1974 | Buckles |
| RE30,046 E | 7/1979 | Van Amerongen |
| 4,743,407 A | 5/1988 | Apel |
| 4,757,812 A | 7/1988 | Arborelius, Jr. |
| 4,832,012 A | 5/1989 | Raabe |
| 4,907,581 A | 3/1990 | King |
| 4,941,618 A | 7/1990 | Hildebrand |
| 5,030,390 A | 7/1991 | Nicholls |
| 5,048,729 A | 9/1991 | Pritchard |
| 5,261,601 A | 11/1993 | Ross |
| 5,277,175 A | 1/1994 | Riggs |
| 5,301,664 A | 4/1994 | Sievers |
| 5,379,760 A | 1/1995 | Ryder |
| 5,431,345 A | 7/1995 | Lund |
| 5,479,920 A | 1/1996 | Piper |
| 5,497,763 A | 3/1996 | Lloyd |
| 5,535,989 A | 7/1996 | Sen |
| 5,544,646 A | 8/1996 | Lloyd |
| 5,545,456 A | 8/1996 | Suida |
| 5,570,682 A | 11/1996 | Johnson |
| 5,603,314 A | 2/1997 | Bono |
| 5,685,291 A | 11/1997 | Marsh |
| 5,718,222 A | 2/1998 | Lloyd |
| 5,724,959 A | 3/1998 | McAughey |
| 5,755,221 A | 5/1998 | Bisgaard |
| 5,810,755 A | 9/1998 | Leveen |
| 5,816,504 A | 10/1998 | Zuckschwerdt |
| 5,823,179 A | 10/1998 | Grychowski |
| 5,833,057 A | 11/1998 | Char |
| 5,855,564 A | 1/1999 | Ruskewicz |
| 5,858,313 A | 1/1999 | Park |
| 5,915,378 A | 6/1999 | Lloyd |
| 5,971,951 A | 10/1999 | Ruskewicz |
| 6,062,212 A | 5/2000 | Davison |
| 6,070,575 A | 6/2000 | Gonda |
| 6,168,140 B1 | 1/2001 | Akazawa |
| 6,230,706 B1 | 5/2001 | Gonda |
| 6,315,272 B1 | 11/2001 | Stanek |
| 6,354,516 B1* | 3/2002 | Patel ................. A61M 15/0045 |
| | | 239/331 |
| 6,467,477 B1 | 10/2002 | Frank |
| D471,626 S | 3/2003 | Terada |
| 6,527,257 B1 | 3/2003 | Schuld |
| 6,530,370 B1 | 3/2003 | Heinonen |
| 6,598,602 B1 | 7/2003 | Sjoeholm |
| 6,606,989 B1 | 8/2003 | Brand |
| 6,647,987 B2 | 11/2003 | Gonda |
| 6,990,975 B1 | 1/2006 | Jones |
| 7,013,894 B2 | 3/2006 | McFarland |
| 7,163,014 B2 | 1/2007 | Nichols |
| 7,246,617 B1 | 7/2007 | Harmer |
| 7,373,938 B2 | 5/2008 | Nichols |
| 7,562,656 B2 | 7/2009 | Gallem |
| 7,634,998 B1 | 12/2009 | Fenley |
| 7,748,382 B2 | 7/2010 | Denyer |
| 7,900,627 B2 | 3/2011 | Aylsworth |
| 7,984,710 B2 | 7/2011 | Von Schuckmann |
| 8,261,738 B2 | 9/2012 | Denyer |
| 8,343,522 B2 | 1/2013 | Pohl |
| 8,371,299 B2 | 2/2013 | Denyer |
| 8,464,706 B2 | 6/2013 | Crockford |
| 8,491,491 B2 | 7/2013 | Haefner |
| 8,607,786 B2 | 12/2013 | Denyer |
| 8,820,316 B2 | 9/2014 | Crockford |
| 8,944,052 B2 | 2/2015 | Osorio |
| 8,960,189 B2 | 2/2015 | Morrison |
| 9,050,424 B2 | 6/2015 | Van Der Mark |
| 9,050,425 B2 | 6/2015 | Van Der Mark |
| 9,060,715 B2 | 6/2015 | Schipper |
| 9,132,244 B2 | 9/2015 | Dyche |
| 9,135,397 B2 | 9/2015 | Denyer |
| 9,352,107 B2 | 5/2016 | Von Hollen |
| 9,494,506 B2 | 11/2016 | Dyche |
| 9,572,944 B2 | 2/2017 | Van Der Sluis |
| 9,586,223 B2 | 3/2017 | Bentvelsen |
| 9,877,509 B2 | 1/2018 | Dai |
| 2002/0073991 A1 | 6/2002 | Gonda |
| 2004/0045546 A1 | 3/2004 | Hirsh |
| 2004/0113292 A1 | 6/2004 | Sadykhov |
| 2004/0123863 A1 | 7/2004 | Wang |
| 2005/0039744 A1 | 2/2005 | Szirmai |
| 2005/0066968 A1 | 3/2005 | Shofner |
| 2006/0231090 A1* | 10/2006 | King ................. A61M 15/0086 |
| | | 128/200.14 |
| 2007/0003603 A1 | 1/2007 | Karandikar |
| 2007/0175476 A1 | 8/2007 | Lipowicz |
| 2008/0082139 A1 | 4/2008 | Means |
| 2008/0216828 A1* | 9/2008 | Wensley ............... A61K 9/0009 |
| | | 128/203.12 |
| 2008/0283049 A1 | 11/2008 | Mahoney |
| 2009/0192443 A1* | 7/2009 | Collins, Jr. .......... A61M 11/005 |
| | | 604/24 |
| 2010/0031964 A1 | 2/2010 | Turek |
| 2010/0078015 A1 | 4/2010 | Imran |
| 2010/0092746 A1 | 4/2010 | Coant |
| 2010/0192321 A1 | 8/2010 | Tuman |
| 2012/0285446 A1* | 11/2012 | Van Der Mark .... A61M 11/005 |
| | | 128/200.14 |
| 2012/0318259 A1 | 12/2012 | Sadykhov |
| 2013/0032153 A1 | 2/2013 | Neely |
| 2013/0220314 A1 | 8/2013 | Bottom |
| 2013/0228169 A1 | 9/2013 | Stangl |
| 2015/0174349 A1 | 6/2015 | Tunnell |
| 2017/0106155 A1* | 4/2017 | Reed ...................... A61M 11/00 |

FOREIGN PATENT DOCUMENTS

| | | |
|---|---|---|
| CA | 2989355 A1 | 1/2017 |
| CN | 205040652 U | 2/2016 |
| DE | 1817899 | 7/1973 |
| EP | 0135390 | 3/1985 |
| EP | 0845220 A1 | 6/1998 |
| EP | 2149359 | 2/2010 |
| EP | 3182847 A1 | 6/2017 |
| EP | 3313214 A1 | 5/2018 |
| EP | 3316713 A2 | 5/2018 |
| EP | 3332657 A1 | 6/2018 |
| FI | 894224 A | 3/1990 |
| GB | 322927 | 12/1929 |
| GB | 2404867 A | 2/2005 |
| JP | H06345194 | 12/1994 |
| WO | 005011 | 8/2000 |
| WO | 0058022 | 10/2000 |
| WO | 0166064 | 9/2001 |

(56) References Cited

FOREIGN PATENT DOCUMENTS

| WO | 2005102428 | 11/2005 |
| WO | 2008048234 | 4/2008 |
| WO | 2010/104018 A1 | 9/2010 |

OTHER PUBLICATIONS

"flat". Merriam-Webster.com. Retrieved Sep. 19, 2016, from http://www.meriam-webster.com/dictionary/flat.

"metallic". Oxforddictionaries.com. Retrieved Sep. 19, 2016, from https://en.oxforddictionaries.com/definition/metallic.

Zadorecki & Flodin, (1985) Surface modification of cellulose fibers. II. The effect of cellulose fiber treatment on the performance of cellulose—polyester composites. Journal of applied polymer science, 30(10), 3971-3983.

* cited by examiner

METHOD AND APPARATUS FOR PRODUCING FINE CONCENTRATED AEROSOL

CROSS-REFERENCE TO RELATED APPLICATIONS

This application is a Continuation-in-Part of U.S. patent application Ser. No. 13/521,718, filed on Jul. 11, 2012 (published as US 20120318259), which is the U.S. National Stage of International Patent Application No. PCT/IL2011/000038, filed on Jan. 12, 2011, which claims the benefit of U.S. Provisional Patent Application No. 61/294,161, filed on Jan. 12, 2010, the contents of each of which are incorporated herein by reference in their entireties.

TECHNICAL FIELD

The present invention relates to a method and apparatus enabling production of ultra-fine and concentrated aerosol from liquids, for various applications, by using rigid porous material, enabling storage and easy streaming of the aerosol (e.g. for inhalation), fast replacement of liquid carrier device and accuracy of output sprayed dose.

BACKGROUND

Nebulizers are commonly used for delivering aerosol medication to patients via the respiratory system. Desirably, for efficient delivery of medication, the droplet diameter of the aerosol should be sufficiently small so as to reach the lungs of the patient without being obstructed by objects or organs (such as, the inner surface of the nozzle in the nebulizer and the mouth cavity perimeters) and large enough so as to remain in the lungs during exhalation.

The main techniques for producing aerosol in nebulizers include vibrating Mesh technology, jet nebulizers and ultrasonic wave nebulizers. Common to these techniques is the challenge to deliver large volume of medication to the patient while keeping the diameter of the droplets within desired limits.

U.S. Pat. No. 2,284,591 discloses a liquid nebulizer device adapted to provide oily compositions specifically to the nose and throat, through preventing their entrance and congestion in the lungs.

U.S. Pat. No. 3,812,854 discloses an ultrasonic nebulizer for atomizing a liquid medicament comprising a porous solid body having a defined intercommunicating pore structure where the diameters of at least 75% of the pore openings is in the range of 0.5 to 5 microns.

U.S. Pat. No. 4,907,581 discloses a disposable radioactive aerosol inhalation apparatus including a lung aerosol unit, which both generates and traps sub-micron particles, on the order of 0.3 micron, for use in diagnostic pulmonary ventilation studies.

U.S. Pat. No. 5,603,314 discloses a filtration device suitable for reducing exhaled particles released by a patient during aerosol inhalation therapy.

U.S. Pat. Nos. 5,755,221 and 7,246,617 disclose inhaling devices.

U.S. Pat. No. 6,070,575 discloses a nozzle for aerosolizing a drug formulation, the nozzle includes a flexible membrane material having a plurality of pores, the pores have an exit aperture diameter in the range of about 0.5 to about 50 microns.

US 2002/0073991 discloses a method of monitoring aerosol delivery efficacy.

US 2007/0175476 discloses an aerosol powder delivery device.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

In some embodiments, there is provided a nebulizer for producing aerosol, comprising a porous medium, wherein the porous medium is rigid, has two flat sides and further comprises: a plurality of pores; a liquid partially adsorbed in the porous medium; and gas, wherein the gas is caged in pores that are vacant of said liquid, wherein the porous medium is configured to act as a pneumatic multi-nozzle atomizing system.

In some embodiments, the nebulizer further comprising a mouthpiece configured to deliver the aerosol to the lungs of a subject by inhalation.

In some embodiments, the aerosol comprises droplets of the liquid, the droplets having an MMAD within the range of 0.3 to 7 microns. In some embodiments, the diameter of said droplets is in the range 0.3 to 1.1 micrometer. In some embodiments, the droplets are having a Geometric Standard Diameter (GSD) within the range of about 2-5 micrometer In some embodiments, the diameter of the pores in the porous medium is below 1 micrometer.

In some embodiments, the porous medium contains at least 10% liquid contents.

In some embodiments, the porous medium has a modulus of rigidity of at least 10 GPa at 25° C.

In some embodiments, the porous medium comprises a metal.

In some embodiments, the nebulizer further comprises a chamber and a path, wherein the path is configured to receive the aerosol from the porous medium and transfer said aerosol to the chamber.

In some embodiments, the nebulizer further comprises means configured for creating a pressure drop between the two flat sides of the porous medium, said means are selected from a piston and a spring, and a vacuum pump. In some embodiments, the means for creating the pressure drop include a piston and a spring connected to the piston, and wherein said means are configured to generate at least two different magnitudes of said pressure drop.

In some embodiments, the nebulizer further comprises a fixture, the fixture comprises a fixture notch, wherein the piston comprises a plurality of piston slots, wherein the fixture notch is configured to adapt to any one of the plurality of piston slots, thereby compressing the spring at a plurality of heights.

In some embodiments, the liquid comprises a pharmaceutical composition.

In some embodiments, the porous medium is disposable.

In some embodiments, the pressure drop is within the range of 600 to 900 mbar. In some embodiments, the aerosol is ultra-fine highly concentrated aerosol comprising at least 109-1011 droplets per cm3.

In some embodiments, there is provided a method for treating a disease or disorder related to the respiratory system in a subject in need thereof, comprising, administering to the subject a pharmaceutical composition for treatment of said disease or disorder by inhalation, using the nebulizer disclosed herein.

In some embodiments, the diameter of the pores of the porous medium is below 1 micrometer.

In some embodiments, there is provided a method for producing aerosol, comprising the steps of providing the nebulizer disclosed herein; and generating a pressure drop across the porous medium, thereby obtaining aerosol.

In some embodiments, the nebulizer further comprises a mouthpiece.

In some embodiments, the nebulizer further comprises a chamber and a path, and the method further comprising the steps of transferring the aerosol from the porous medium and to the chamber through the path; and storing the aerosol in the chamber.

In some embodiments, the method further comprises the step of positioning the mouthpiece in a position that exposes the aerosol in the chamber to the outer environment.

In some embodiments, there is provided a method for producing aerosol, comprising the steps of providing the nebulizer as disclosed herein, the nebulizer comprise means for creating the pressure drop include a piston and a spring connected to the piston, and wherein said means are configured to generate at least two different magnitudes of said pressure drop, and further comprises a fixture, the fixture comprises a fixture notch, wherein the piston comprises a plurality of piston slots, wherein the fixture notch is configured to adapt to any one of the plurality of piston slots, thereby compressing the spring at a plurality of heights;

electing a piston slot from the plurality of piston slots;

engaging the fixture notch with the elected piston slot, thereby compressing the spring to a height corresponding to said piston slot, generating a pressure drop across the porous medium (by releasing the fixture notch from the piston slot) and producing aerosol, wherein the pressure drop being proportional to the height of the elected piston slot.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 1 schematically illustrates a cross section of a porous medium, in accordance with some embodiments;

FIG. 2*a* schematically illustrates a cross-section of a nebulizer with a porous medium, in accordance with some embodiments;

FIG. 2*b* schematically illustrates a cross-section of a nebulizer with a porous medium, in accordance with some embodiments;

FIG. 2*c* schematically illustrates a cross-section of a nebulizer with a porous medium, in accordance with some embodiments;

FIG. 2*d* schematically illustrates a cross-section of a nebulizer with a porous medium, in accordance with some embodiments;

FIG. 3 schematically illustrates a cross-section of a nebulizer with a porous medium, in accordance with some embodiments.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The proposed technology is intended for creating ultra-fine aerosol, which is specifically beneficial for delivering pharmaceutically active ingredients to the lungs, including the alveoli, of a subject in need of a treatment to their respiratory system, through inhalation. Generally, the formation of ultra-fine aerosol (typically, 0.3 to 1.1 micrometer of droplet size of the aerosol) is achieved by using rigid porous material into which a liquid comprising the pharmaceutically active ingredients, is partially adsorbed. The porous medium acts as a pneumatic multi-nozzle atomizing system.

In some embodiments, there is provided a nebulizer for producing aerosol, comprising a porous medium, wherein the porous medium is rigid, has two flat sides and further comprises: a plurality of pores; a liquid partially adsorbed in the porous medium; and gas, wherein the gas is caged in pores that are vacant of said liquid, and wherein the porous medium is configured to act as a pneumatic multi-nozzle atomizing system.

The nebulizer disclosed herein may function as an inhaler under some circumstances. Thus, the terms ‘nebulizer’ and ‘inhaler’ as used herein may be interchangeable.

Advantageously, the nebulizer disclosed herein prevents accumulation or formation “dead” volume of atomized liquid, during aerosol generation, which cannot be sprayed as aerosol.

An additional benefit of the nebulizer disclosed herein is that it may be used (held) in any orientation, during its operation. The formation of aerosol in the required dosage is not affected by the position or orientation of the nebulizer, during usage.

Furthermore, unlike use of a mask, tent or any disperser, use of the nebulizer disclosed herein does not involve medicine leakage. Thus, use of the nebulizers disclosed herein is safer and effective to the patients and the environment.

Another advantage conferred by use of the nebulizer is that no heating nor ultrasonic energy is required for its operation. Thus, the nebulizer is safe and effective for any pharmaceuticals, including heat/radiation sensitive pharmaceutical compositions.

In some embodiments, the nebulizer is configured to deliver the aerosol to the lungs by inhalation. In some embodiments, the nebulizer is configured to deliver the aerosol to a subject's lungs by inhalation. In some embodiments, the nebulizer is configured to prevent substantially the delivery of the aerosol to subject's nose and/or throat.

The correlation between droplet size and deposition thereof in the respiratory system has been established. It is generally known in the art that large droplets which are intended for delivery of therapeutics to the nose and throat, and not to the lungs, should be in the size of above 5 micrometers in diameter (see, for example, Natural Ventilation for Infection Control in Health-Care Settings, Atkinson et al. World Health Organization 2009, p. 103 lines 15-18). Droplets around 10 micron in diameter are suitable for deposition in the oropharynx and the nasal area; while droplets around 2-4 micron in diameter are suitable for deposition in the central airways, including the lungs, alveoli, bronchi and alveolar ducts. As a result, a nebulizer configured for producing aerosol having a diameter lower than 5 micrometer may enhance lung congestion at the expense of delivery to the nose and/or throat.

As used herein, the term "respiratory system" refers to the system of organs in the body responsible for the intake of oxygen and the expiration of carbon dioxide. The system generally includes all the air passages from the nose to the pulmonary alveoli. In mammals it is generally considered to include the lungs, bronchi, bronchioles, trachea, nasal passages, and diaphragm.

In some embodiments, the aerosol comprises droplets. In some embodiments, the aerosol comprises droplets of the liquid. In some embodiments, the nebulizer produces the aerosol from the liquid.

It was found that nebulization of liquids using nebulizers as disclosed herein, results in droplets having a mass median aerodynamic diameter (MMAD) sufficiently small so as to reach the lungs, rather than precipitate on their way thereto. The small droplets reaching the lungs enable efficient respiratory delivery of therapeutic agents in the aerosolized liquid. This is an overall advantage as maximizing the delivery of therapeutic agents to the lungs, while minimizing their deposition in the mouth and throat are important in treating diseases or disorders related to the respiratory system.

The terms 'droplet size' and 'mass median aerodynamic diameter', also known as MMAD, as used herein are interchangeable. MMAD is commonly considered as the median particle diameter by mass. MMAD may be evaluated by plotting droplet size vs. the cumulative mass fraction (%) in the aerosol. MMAD may then be determined according to the interpolated droplet size corresponding to the point, where the cumulative mass fraction is 50%. This point represents the estimated values of particle sizes, above which the droplets are responsible to half to masses and below, which the droplets are responsible to the other halves, in each solution.

In some embodiments, the MMAD is within the range of 2 to 10 microns. In some embodiments, the aerosol comprises droplets having an MMAD of less than 10 microns. In some embodiments, the aerosol comprises droplets having an MMAD within the range of 0.3 to 7 microns. In some embodiments, the MMAD is less than 5 microns.

In some embodiments, the diameter of the droplets is in the range 0.1 to 2.5 micrometer. In some embodiments, the diameter of the droplets is in the range 0.1 to 1.5 micrometer. In some embodiments, the diameter of the droplets is in the range 0.3 to 1.1 micrometer. In some embodiments, the diameter of the droplets is in the range 0.5 to 1.0 micrometer.

In some embodiments, the aerosol comprises droplets having a Geometric Standard Diameter (GSD) within the range of about 0.4-7 micrometer. In some embodiments, the aerosol comprises droplets having a GSD within the range of about 2-5 micrometer.

In some embodiments, the diameter of the pores in the porous medium is below 2 micrometer. In some embodiments, the diameter of the pores in the porous medium is below 1 micrometer. In some embodiments, the diameter of the pores in the porous medium is below 0.75 micrometer. In some embodiments, the diameter of the pores in the porous medium is below 0.5 micrometer. In some embodiments, the diameter of the pores in the porous medium is below 0.25 micrometer. In some embodiments, the diameter of the pores in the porous medium is below 0.1 micrometer.

The term "partially absorbed" as used herein refers to the percentage of liquid absorbed in the pores of the porous medium, wherein 0% refers to a porous medium where all of its pores are vacant of liquid. Thus, the term "partially absorbed" may refer to a porous medium wherein at least 0.005% of the pores contain liquid, or wherein the overall contents of the vacant space within the porous medium occupied with liquid is 0.005%. In some embodiments, partially absorbed refers to at least 0.001% liquid contents within the porous medium. In some embodiments, partially absorbed refers to at least 0.05% liquid contents within the porous medium. In some embodiments, partially absorbed refers to at least 0.01% liquid contents within the porous medium. In some embodiments, partially absorbed refers to at least 0.5% liquid contents within the porous medium. In some embodiments, partially absorbed therein refers to at least 0.1% liquid contents within the porous medium. In some embodiments, partially absorbed refers to at least 1% liquid contents within the porous medium. In some embodiments, partially absorbed refers to at least 5% liquid contents within the porous medium. In some embodiments, partially absorbed refers to at least 10% liquid contents within the porous medium. In some embodiments, partially absorbed refers to at least 20% liquid contents within the porous medium. In some embodiments, partially absorbed refers to at least 30% liquid contents within the porous medium. In some embodiments, partially absorbed refers to at least 40% liquid contents within the porous medium. In some embodiments, partially absorbed refers to at least 50% liquid contents within the porous medium.

In some embodiments, the term "partially absorbed" may refer to the content of liquid within the volume of pores located on the surface and in the immediate vicinity of the surface (sub surface) of a porous medium. In some embodiments, the volume of the sub-surface may extend from the surface to a depth of about 50 micron from the surface.

In some embodiments, partially absorbed refers to a porous medium wherein at least 0.5% of the surface and sub-surface pores contain liquid. In some embodiments, partially absorbed refers to at least 1% liquid contents within the surface and sub-surface pores. In some embodiments, partially absorbed refers to at least 10% liquid contents within the surface and sub-surface pores. In some embodiments, partially absorbed refers to at least 20% liquid contents within the surface and sub-surface pores. In some embodiments, partially absorbed refers to at least 30% liquid contents within the surface and sub-surface pores. In some embodiments, partially absorbed refers to at least 40% liquid contents within the surface and sub-surface pores. In some embodiments, partially absorbed refers to at least 50% liquid contents within the surface and sub-surface pores. In some embodiments, partially absorbed refers to at least 60% liquid contents within the surface and sub-surface pores.

In some embodiments, the porous medium is rigid when liquid is partially adsorbed therein.

The term "rigid" as used herein characterizes materials that are generally non-flexible, and do not undergo deformation in response to an applied force. Specifically, a porous medium that is rigid, does not bend or otherwise deforms upon ejection of liquid droplets therethrough. Rigidity is typically measured in pressure units, through parameters such as Modulus of Rigidity (G; Shear Modulus) or Young's modulus. Rigidity of materials may be dependent on environments features. For example, cellulose may exhibit a rigid structure in a dry form, however, when adsorbed in liquid cellulose cannot maintain a dry rigid structure, but rather becomes flexible. Glass and most metals are rigid in a wide range of temperature, including at room temperature, but become flexible in extremely high temperatures.

In some embodiments, the rigid porous medium does not substantially change its rigidity upon adsorption of liquids therein. In some embodiments, the rigidity of the rigid porous medium is not substantially effected upon being in contact with liquids.

In some embodiments, porous medium is made of a rigid material, wherein the rigidity of the rigid material is not substantially effected by contact with liquids.

In some embodiments, the porous medium has a modulus of rigidity of at least 10 GPa ($10^9$ pascal) at 25° C. In some embodiments, the porous medium has a modulus of rigidity of at least 15 GPa at 25° C. In some embodiments, the porous medium has a modulus of rigidity of at least 20 GPa at 25° C. In some embodiments, the porous medium is substantially devoid of materials having modulus of rigidity lower than 10 GPa at 25° C.

As used herein, the terms "substantially effected" and "substantially change", when referring to the rigidity of materials, are intended to include changes of more than 10% in the modulus of rigidity of the material. For example, for a dry porous medium having a modulus of rigidity of 50 GPa, the phrase "the rigidity of the porous medium is not substantially effected by contact with liquids" means that upon contact with liquids, the modulus of rigidity of the material will remain in the range of 45 GPa to 55 GPa.

In some embodiments, the porous medium is made of a material selected from the group consisting of metals and metal alloys. In some embodiments, the porous medium comprises a metal. In some embodiments, the porous medium is made of metal. In some embodiments, the porous medium comprises polymers.

It is to be understood that a polymer used for forming the porous medium is typically a rigid polymer, such as, a polymer having a Tg (glass transition temperature) in the range of 100 or above 100.

In some embodiments, the porous medium comprises materials selected from the group consisting of aluminum, cobalt, copper, iron, magnesium, nickel, silicon, steel, titanium, polymers, including alloys and combinations thereof.

In some embodiments, the porous medium is rigid and has two flat sides. It is to be understood that, due to the rigidity of the porous medium, it remains flat throughout the operation of the nebulizer. As defined above, a rigid medium is resistant to deformation upon application of external force. Therefore, the medium does not curve into a concave or convex shape, rather it remains flat during operation of the nebulizer, and specifically, during formation of aerosol.

In some embodiments, the nebulizer further comprises a chamber and a path, wherein the path is configured to receive the aerosol from the porous medium and transfer said aerosol to the chamber.

In some embodiments, the nebulizer further comprises an outlet, also referred to as exit hole. In some embodiments, the outlet is configured to release said aerosol by inhalation. In some embodiments, the outlet is configured to deliver said aerosol to the lungs by inhalation.

In some embodiments, the nebulizer further comprises a cover configured to fix the porous medium to the body of the nebulizer.

In some embodiments, the cover further comprises a duct extended between the cover and the external environment.

In some embodiments, the duct is open, such that the internal environment of the nebulizer is exposed to the atmospheric pressure. Without being bound by any theory or mechanism, by maintaining the duct open, the internal pressure within the nebulizer reaches a steady state of atmospheric pressure.

In some embodiments, the nebulizer further comprises means for creating a pressure drop between the two flat sides of the porous medium. In some embodiments, the nebulizer further comprises an element configured for creating a pressure drop between the two flat sides of the porous medium. In some embodiments, the element comprises a piston and a spring. In some embodiments, the element further comprises a vacuum pump. In some embodiments, the element further comprises a piston, a spring and vacuum pump.

In some embodiments, creating a pressure drop between the two flat sides of the porous medium is achieved by introducing pressurized air to one flat side of the porous medium. In some embodiments, creating a pressure drop between the two flat sides of the porous medium comprises introducing vacuum or sub-atmospheric pressure near one flat side of the porous medium. In some embodiments, creating a pressure drop between (or across) the two flat sides of the porous medium comprises generating or having a pressure difference between the two flat sides (or flat surfaces) of the rigid porous medium. In some embodiments, the pressure difference is in the range of 600 mbar to 900 mbar.

In some embodiments, prior to the pressure drop, the pressure across the porous medium is an atmospheric pressure. In some embodiments, the pressure drop across the porous medium is within the range of 500 to 990 mbar. In some embodiments, the pressure drop is within the range of 600 to 900 mbar. In some embodiments, the pressure drop is within the range of 650 to 850 mbar.

In some embodiments, the porous medium is in a shape of a disc.

In some embodiments, the porous medium is in a shape of a pill.

In some embodiments, the porous medium is in a shape of a coin.

In some embodiments, the porous medium is in a shape of a cylinder.

In some embodiments, the nebulizer further comprises a tube connecting the chamber to said duct and configured to increase the pressure drop between the two flat sides of the porous medium.

In some embodiments, the nebulizer further comprises a fixture and a piston connected to a spring, the fixture comprising a fixture notch, and the piston comprising at least two piston slots located at different levels along the piston. In some embodiments, the fixture is connected to the peripheral surface of the outer structure, optionally through a joint, wherein the joint serves as a rotation axis and one end of the fixture is further attached to the peripheral surface of the outer structure in order to force the other end of the fixture, comprising the fixture notch, to be engaged with any one of the piston slots. In some embodiments, applying pressure to the fixture at the region of the fixture spring causes the fixture to rotate against the joint, thereby releasing (displacing) the fixture notch from any one of the piston slots. In some embodiments, the displacement of the fixture notch releases the spring along a given height, depending on the piston slot from which the fixture notch has been released. Thus, displacement of the fixture notch can release the spring along various heights, thereby generating different magnitudes of pressure drop across the porous medium for, depending on the position (level or height relative to the dimension of the nebulizer) of the piston slot. The terms "height" and "heights" as used herein generally refer to the distance between the bottom of the nebulizer's body (also termed outer structure 101 in FIGS. 2a-2d) and the piston.

In some embodiments, the liquid comprises water. In some embodiments, the liquid comprises an aqueous pharmaceutically suitable carrier and at least one pharmaceutical active ingredient. In some embodiments, the liquid comprises an aqueous dispersion. In some embodiments, the liquid comprises any one of an aqueous solution, an aqueous emulsion, an aqueous suspension and an aqueous colloidal suspension.

In some embodiments, the liquid comprises a pharmaceutical composition.

As used herein, the term "pharmaceutical composition" is interchangeable with any of the terms "medication", "drug" and the like, refers to a preparation of a composition comprising one or more pharmaceutically active agents, suitable for administration to a patient via the respiratory system.

In some embodiments, the liquid comprises a therapeutically effective amount of a pharmaceutical composition. In some embodiments, the liquid comprises a pharmaceutical composition for treatment or prevention of a disease or disorder of the respiratory system.

In some embodiments, the aerosol comprises a pharmaceutical composition. In some embodiments, the aerosol comprises a therapeutically effective amount of the pharmaceutical composition. In some embodiments, the aerosol comprises a pharmaceutical composition for treatment or prevention of a disease or disorder of the respiratory system.

As used herein, the term "therapeutically effective amount" refers to a pharmaceutically acceptable amount of the pharmaceutical composition, or the pharmaceutical active ingredient(s), which prevents or ameliorates, at least partially, the symptoms signs of a particular pulmonary or respiratory disease or disorder, in a living organism to whom it is administered over some period of time.

In some embodiments, the pharmaceutical composition is for the treatment of a respiratory disease or disorder. In some embodiments, the disease or disorder is selected from the group consisting of asthma, bronchitis, emphysema, lung infection, cystic fibrosis, AAT deficiency, COPD, ARDS, IRDS, BPD, and MAS. Each possibility is a separate embodiment of the invention.

In some embodiments, the disease or disorder is affecting the airways, the alveoli or the interstitium, such as, asthma, chronic obstructive pulmonary disease, chronic bronchitis, emphysema, acute bronchitis, cystic fibrosis, pneumonia, tuberculosis, fragile connections between alveoli, pulmonary edema, lung cancer in its many forms, acute respiratory distress syndrome, pneumoconiosis, mouth and pharynx cancer, tracheal tumors and interstitial lung disease among others.

As used herein the term "aerosol" or "aerosolized agent" refers to a suspension of solid or liquid particles of the agent in a gas. As used herein "aerosol" or "aerosolized agent" may be used generally to refer to an agent, including, a pharmaceutically active agent, that has been vaporized, nebulized, or otherwise converted from a solid or liquid form to an inhalable form including suspended solid or liquid drug particles.

In some embodiments, the liquid further comprises at least one pharmaceutical acceptable carrier. In some embodiments, the liquid may further comprise one or more stabilizers.

In some embodiments, the liquid further comprises a sweetener. In some embodiments, the sweetener is selected from the group of artificial sweeteners including saccharine, aspartame, dextrose and fructose.

In some embodiments, the liquid further comprises at least one anti-coughing agent.

The term "anti-coughing agent" as used herein refers to an active agent used for the suppression, alleviation or prevention of coughing and irritations and other inconveniencies in the large breathing passages that can, or may, generate coughing. Anti-coughing agent include, but are not limited to antitussives, which are used for which suppress coughing, and expectorants, which alleviate coughing, while enhancing the production of mucus and phlegm. Anti-coughing agents may ease the administration of inhaled aerosols.

In some embodiments, the at least one anti-coughing agent is selected from expectorants, antitussives or both. In some embodiments, the at least one anti-coughing agent is selected from the group consisting of menthol, dextromethorphan, dextromethorphan hydrobromide, hydrocodone, caramiphen, dextrorphan, 3-methoxymorphinan or morphinan-3-ol, carbetapentane, codeine, acetylcysteine and combinations thereof.

In some embodiments, the liquid further comprises at least one preservative. In some embodiments, the preservative is selected from the group consisting of benzyl alcohol, propylparaben, methylparaben, benzalkonium chloride, phenyl ethyl alcohol, chlorobutanol, potassium sorbate, phenol, m-cresol, o-cresol, p-cresol, chlorocresol and combinations thereof.

In some embodiments, the porous medium is disposable.

In some embodiment, the porous medium is configured to multiple uses. It is to be understood, that multiple use may require washing the porous medium between uses.

In some embodiments, the nebulizer is mobile. In some embodiments, the nebulizer is portable. In some embodiments, the nebulizer is handheld. In some embodiments, the nebulizer is powered by a mobile power source.

In some embodiments, the nebulizer is configured to communicate with servers, databases, personal devices (computers, mobile phones) among others.

In some embodiments, the nebulizer is configured to communicate wirelessly with servers, databases, personal devices (computers, mobile phones) among others.

In some embodiments, the nebulizer further comprises at least one tubular opening, also termed herein "mouthpiece" configured to deliver the aerosols to a respiratory system of a subject, and an outer structure opening configured to expose the contents of the chamber to the mouthpiece. In some embodiments, the mouthpiece extends outwardly from the lower peripheral surface of the outer structure towards the environment outside the nebulizer, or towards the user. In some embodiments, the mouthpieces is, configured to rotate around said peripheral surface from a first opening position to a second opening position. In first opening position the mouthpiece is positioned against a wall of the outer structure, where in second opening position the mouthpiece is positioned against the outer structure opening. In first opening position, both the mouthpiece and the outer structure opening are blocked, such that the mouthpiece is exposed to the outer environment but blocked by the wall of the outer structure to the contents of the chamber. Similarly, the outer structure opening is blocked from the outer environment. Blocking of the outer structure can be, for example by means of a ring. In some embodiments, the ring is connected to the mouthpiece and is configured to rotate around the periphery of the outer structure, the ring being open only at the region of connection with the mouthpiece. In the second opening position, the aerosol contained within the chamber is exposed, through the outer structure opening, followed by the mouthpiece, to the outer environment.

In some embodiments there is provided a method of delivering a pharmaceutical composition to a subject by inhalation, the method comprising administering the pharmaceutical composition to the subject using the nebulizer disclosed herein.

In some embodiments there is provided a method of delivering a pharmaceutical composition to a subject in need thereof by inhalation, the method comprising administering the pharmaceutical composition to the subject using the nebulizer disclosed herein.

In some embodiments, administering the pharmaceutical composition to the subject comprises delivering the pharmaceutical composition in the form of aerosols to the respiratory system of the subject.

In some embodiments, the subject in need thereof is a subject afflicted with respiratory disease or disorder.

In some embodiments there is provided a porous medium configured to act as a pneumatic multi-nozzle atomizing system, wherein the porous medium is rigid, has two flat sides and further comprises a plurality of pores; a liquid partially adsorbed in the porous medium; and gas, wherein the gas is caged in pores that are vacant of said liquid.

In some embodiments, the porous medium is configured to release an aerosol. In some embodiments, the aerosol comprises droplets. In some embodiments, the aerosol comprises droplets of the liquid.

In some embodiments, the MMAD is within the range of 2 to 10 microns. In some embodiments, the aerosol comprises droplets having an MMAD of less than 10 microns.

In some embodiments, the aerosol comprises droplets having an MMAD within the range of 0.3 to 7 microns. In some embodiments, the MMAD is less than 5 microns. In some embodiments, the diameter of the droplets is in the range 0.1 to 2.5 micrometer. In some embodiments, the diameter of the droplets is in the range 0.1 to 1.5 micrometer. In some embodiments, the diameter of the droplets is in the range 0.3 to 1.1 micrometer. In some embodiments, the diameter of the droplets is in the range 0.5 to 1.0 micrometer. In some embodiments, the aerosol comprises droplets having a Geometric Standard Diameter (GSD) within the range of about 0.4-7 micrometer. In some embodiments, the aerosol comprises droplets having a GSD within the range of about 2-5 (two to five) micrometer.

In some embodiments, the porous medium is in a flat shape selected from the group consisting of: cylinder, ring, disc and coin.

In some embodiments, the liquid comprises a pharmaceutical composition. In some embodiments, the aerosol comprises a pharmaceutical composition for treatment of a disease or disorder of the respiratory system. In some embodiments, the pharmaceutical composition is intended for delivery to the lungs.

In some embodiments, there is provided a method for producing ultra-fine highly concentrated aerosol, comprising providing the nebulizer disclosed herein and inducing a pressure drop between the two flat sides of the porous medium, thereby producing aerosol.

In some embodiments, inducing a pressure drop between the two flat sides of the porous medium comprises introducing pressurized air to one flat side of the porous medium.

In some embodiments, inducing a pressure drop between the two flat sides of the porous medium comprises introducing vacuum or sub-atmospheric pressure near one flat side of the porous medium.

In some embodiments, inducing a pressure drop between the two flat sides of the porous medium comprises connecting the nebulizer to a pump.

In some embodiments, inducing a pressure drop between the two flat sides of the porous medium comprises displacing the piston. In some embodiments, inducing a pressure drop between the two flat sides of the porous medium comprises manually displacing the piston. In some embodiments, the outer structure includes an elongated slot through which an extension arm, connected to the piston, protrudes outwardly. In some embodiments the extension arm is displaced in the elongated direction along the outer structure, such that manual displacement of said extension arm, for example by the user's hand, in the upward or downward direction, displaces the piston located in the chamber of the outer structure in the same direction. In that manner, after the release of the piston and its movement downward by the force exerted by the spring, as described hereinabove, the user is able to manually push the extension arm upwards while compressing the fixture spring, releasing the fixture when the fixture notch is placed against the desired height level of the piston slot, rendering the nebulizer ready for reuse.

The term "concentrated aerosol" as used herein refers to the number of droplets per volume unit. Concentrated aerosols include more than $10^8$ droplets per $cm^3$. Highly concentrated aerosol includes more than $10^9$ droplets per $cm^3$.

In some embodiments, the aerosol includes more than $10^9$ droplets per $cm^3$. In some embodiments, the aerosol includes more than $10^9$-$10^{11}$ droplets per $cm^3$.

In some embodiments, inducing the pressure drop is achieved by inducing a pressure drop on one side of said two flat sides of the porous medium.

In some embodiments, inducing the pressure drop is achieved by vacuum generating means comprising a piston.

In some embodiments, pressure drop across the porous medium is within the range of 500 to 990 mbar; 600 to 900 mbar; or 650 to 850 mbar.

In some embodiments, the method further comprises storing the aerosol in the chamber.

In some embodiments, the method further comprises storing the aerosol in the chamber under vacuum.

In some embodiments, the aerosol is transferred under vacuum in the chamber for storage.

Reference is now made to FIG. 1, which schematically illustrates a cross section of porous medium 102. Porous medium 102 comprises rigid porous material 1, pores 2, liquid 3 and gas 4, according to some embodiments.

Liquid 3 is contained within some of pores 2 of porous medium 102, according to some embodiments. It is intended for spraying from a nebulizer, such as nebulizer 100 of FIGS. 2a-2d, which includes porous medium 102, according to some embodiments. Liquid 3 is partially absorbed in porous material 1, according to some embodiments. Liquid 3 includes an aqueous pharmaceutical composition, comprising medication for the treatment of a pulmonary disease, and is intended for spraying through a nebulizer into the lungs, according to some embodiments.

Pores 2 are being cavities within rigid porous material 1, according to some embodiments. Pores 2 are of sub-micron size, i.e. their median diameter is below 1 micrometer, according to some embodiments. Pores 2 are partially adsorbed by liquid 3 and partially filled with gas 4, according to some embodiments. Pores 2 are acting as nozzles, according to some embodiments.

Gas 4 is caged in some of pores 2, which are vacant of liquid 3, according to some embodiments.

Figure 2A:
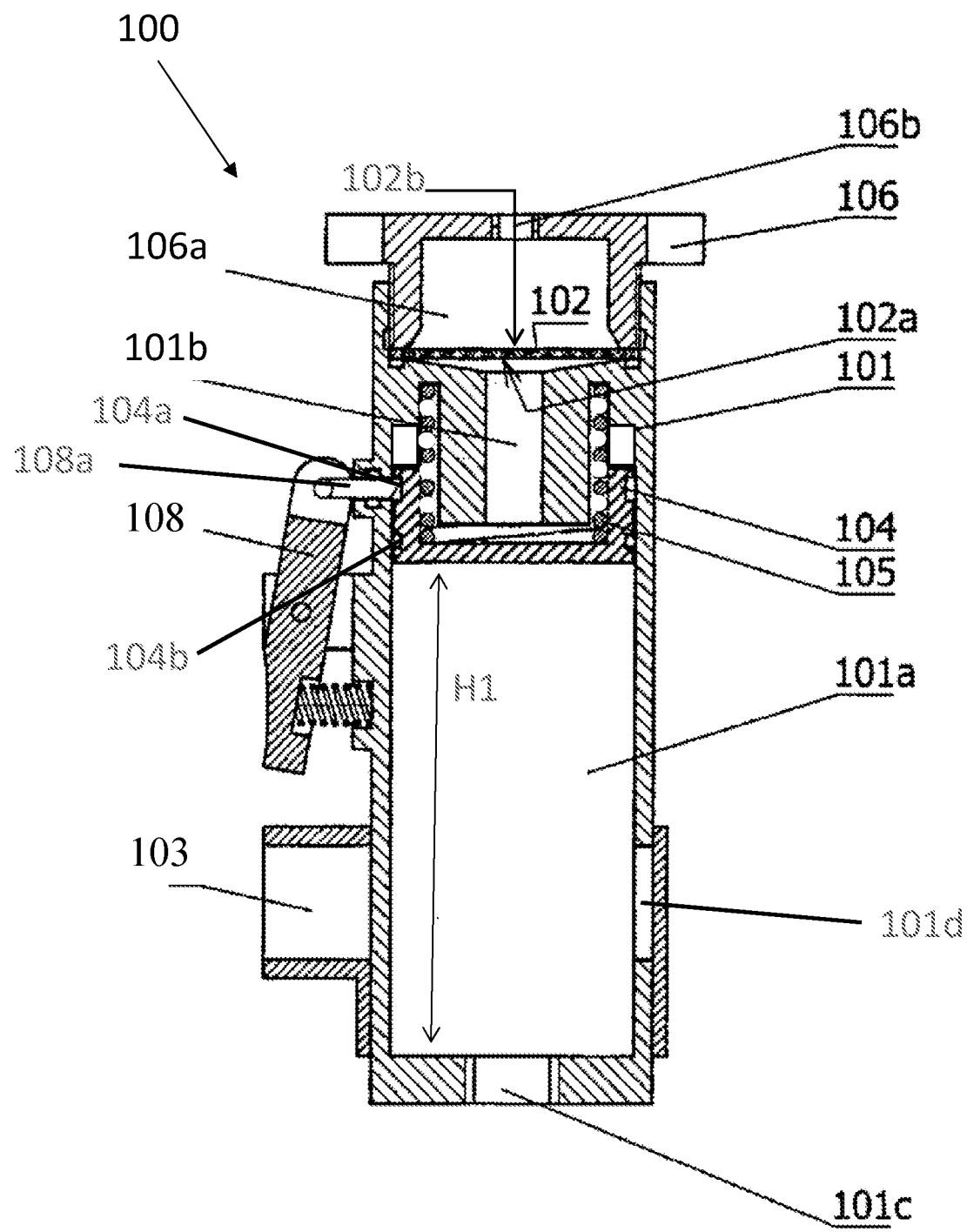
Figure 2B:
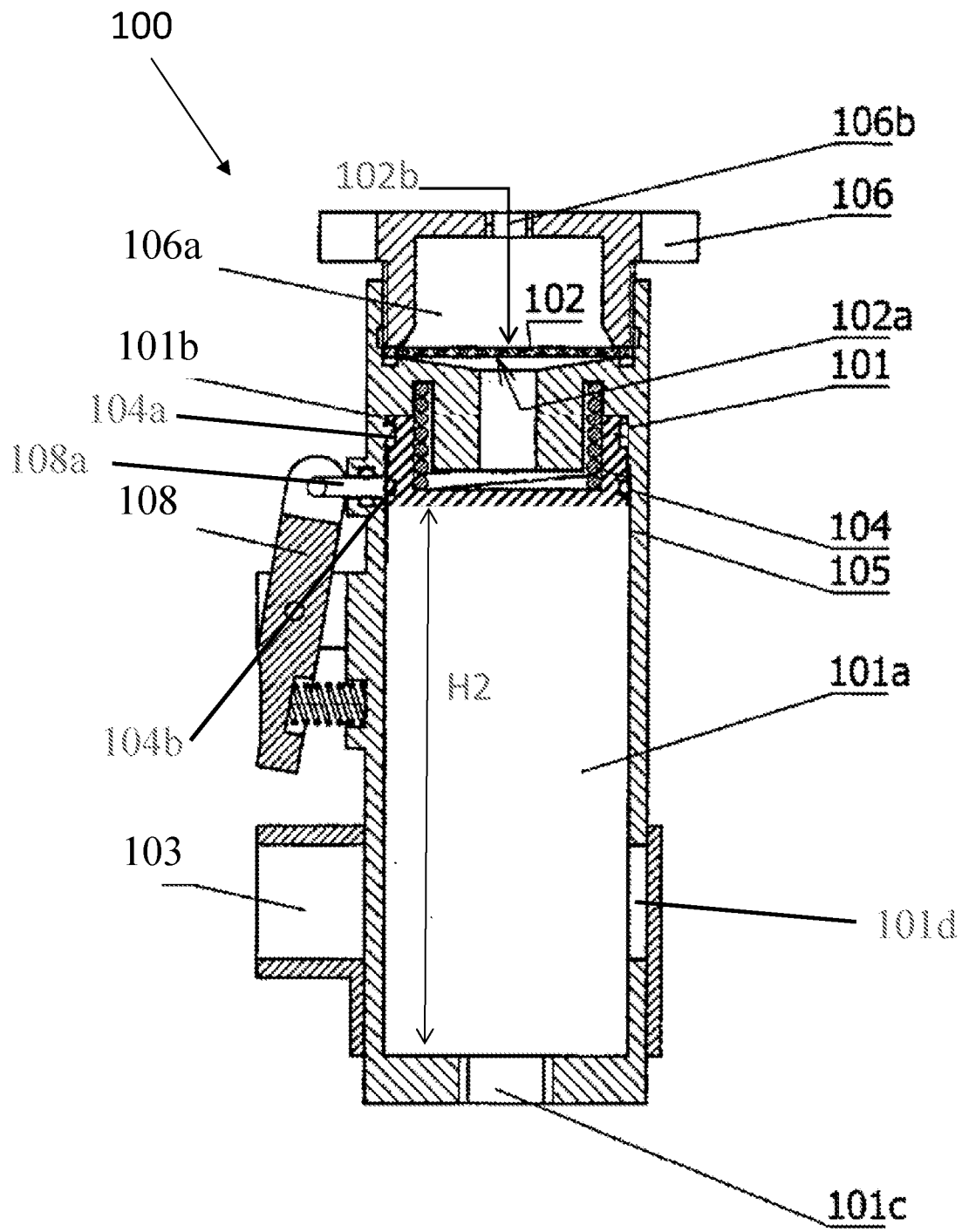
Figure 2C:
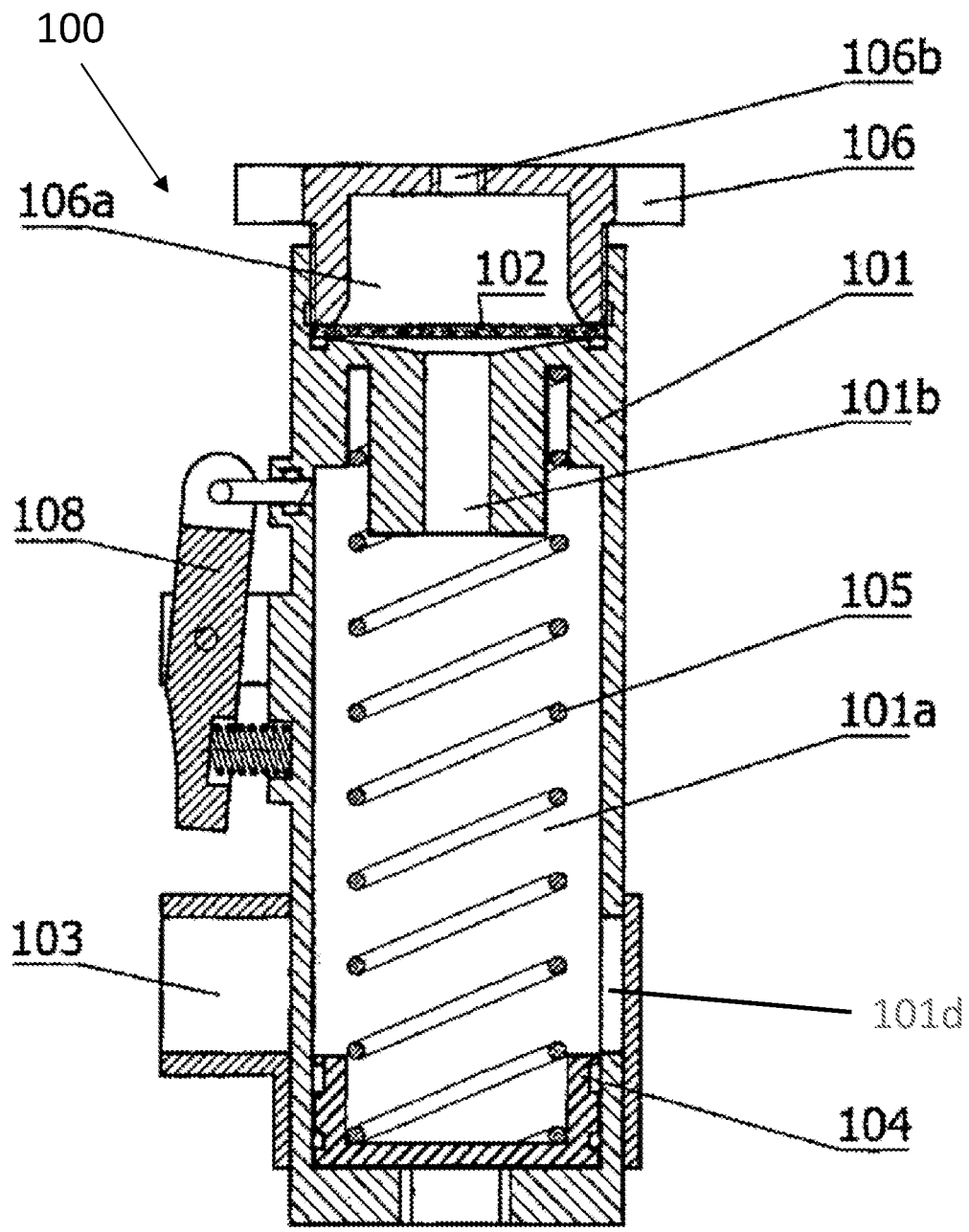

Porous material 1 form the body of porous medium 102, according to some embodiments. It is a rigid metallic material, which is shaped as a coin, according to some embodiments. Porous material 1 has structure and dimensions, which are determined according to the required aerosol characteristics for each required application, according to some embodiments. For example, the dispersing area of porous material 1 (i.e. the surface area, or one side, of porous material 1) determines the quantity of achieved aerosol. The greater the surface area, the more aerosol is produced, per use. Reference is now made to FIGS. 2a-2d, which schematically illustrate cross-sectional views of a nebulizer 100 comprising porous medium 102, according to some embodiments. Specifically, FIGS. 2a-c illustrate nebulizer 100 comprising porous medium 102, in different stages: FIGS. 2a-2b illustrate nebulizer 100 comprising porous medium 102 prior to aerosol production, in a first optional compressed position and a second optional compressed position, respectively; FIG. 2c illustrates nebulizer 100 comprising porous medium 102 when nebulizer 100 is in aerosol production position, due to the pressure drop generated between upper flat side 102b and lower flat side 102a of the porous medium 102; and FIG. 2d describes nebulizer 100 comprising porous medium 102 in a position that enables aerosol inhalation.

Nebulizer 100 is configured to transform liquid 3 to an aerosol, according to some embodiments. The aerosol spraying is performed by instantaneously inducing pressure drop across the thickness of porous medium 102, according to some embodiments. Since porous medium 102 is has a thickness and two flat sides, the differential pressure occurs between the two flat sides of porous medium 102, according to some embodiments. When porous medium 102 is in atmospheric pressure, a pressure drop is induced across porous medium 102, creating a low pressure at one side of porous medium 102, compared to the atmospheric pressure on the other side of porous medium 102, according to some embodiments. According to some embodiments, the size of the pressure drop may be in the range of 600 to 900 mbar. Nebulizer 100 being under a pressure drop across porous medium 102 is illustrated in FIG. 2c. At this stage, atomization occurs as a result of the pressure difference across the two sides of porous medium 102, according to some embodiments. The pressure difference causes the medium to act as a pneumatic multi-nozzle, where the nozzles are defined by pores 2 of porous medium 102, according to some embodiments.

Without wishing to be bound by any theory or mechanism of action, the effect of pneumatic multi-nozzle atomization is the result of gas 4, which is caged in the internal volume of porous medium 102, being released in the direction of vacuum or low pressure. Gas 4 release causes pores 2 to act as nozzles and spray liquid 3 outside porous medium 102. The aerosol is then achieved on the side of the lower pressure—bottom flat side 102a, as illustrated in FIG. 2a. This mechanism of nebulizing action does not require an external gas supply in order to achieve aerosol formation.

The pressure drop is the result of the difference between an atmospheric pressure above porous medium 102 and the lower pressure generated in the chamber below porous medium 102, also referred to as aerosol accumulator, or vacuum accumulator 101a. Vacuum accumulator 101a is also used for storing the aerosol, after being produced, until the aerosol is required for use (i.e. inhalation), according to some embodiments.

According to some embodiments, the low pressure generated in the aerosol accumulator (vacuum accumulator 101a) is sub-atmospheric pressure.

According to some embodiments, the low pressure generated in aerosol accumulator (vacuum accumulator 101a) is vacuum or negative pressure.

Vacuum accumulator 101a may also be used as a drying chamber depending on the relation between the volume of accumulator 101a and the quantity of the droplets, and further depending on the overall parameters of the environment inside vacuum accumulator 101a, according to some embodiments. Such parameters include temperature and pressure. Upon using chamber 101a for drying, dry aerosol is obtained by nebulizer 100, according to some embodiments.

In addition, drying process can take place by the act of inhalation itself, when the inhaled air acts as drying agent, according to some embodiments.

Nebulizers comprising porous medium 102, such as nebulizer 100, operate in many different environments and any positions, such as, in an upright and horizontal position, according to some embodiments.

According to some embodiments, nebulizer 100 may be self-sustained, i.e. the pressure drop is created inherently and not by connecting nebulizer 100 to a pump.

Porous medium 102 may also be used as a storage container for liquid 3 prior to the conversion of liquid 3 to aerosol, according to some embodiments. Porous medium 102 as a storage container may include porous medium 102 soaked with a pre-determined quantity of liquid 3, according to some embodiments.

According to some embodiments, porous medium 102 is soaked with a pre-determined quantity of liquid 3, forming a ready for use "pill". According to some embodiments, the pill is hermetically and sterilely sealed and packed.

According to some embodiments, porous medium 102 is packed together with a container containing liquid 3, where in between porous medium 102 and the container, there is a buffer layer impermeable to liquids. This packing forms a "sandwich" like device. Upon removal of the buffer layer, porous medium 102 absorbs liquid 3. According to some embodiments, removal of the buffer layer from the sandwich pack is performed prior to use of nebulizer 100 or porous medium 102, i.e. before the atomizing effect takes place in order to perform aerosol.

According to some embodiments, the sandwich is sealed and packed. In some embodiments, the sandwich is disinfected and sterilized prior to being sealed and packed.

According to some embodiments, porous medium 102 is designed to be used with specific nebulizer devices, and may be adapted to use with any nebulizer, if required.

According to some embodiments, porous medium 102 is disposable.

According to some embodiments, porous medium 102 is configured for multiple uses. According to some embodiments, porous medium 102 is configured for discharge of, and replenishment with, liquid 3.

According to some embodiments, nebulizer 100 further comprises an outer structure 101. Outer structure 101 encompasses vacuum accumulator 101a. The dimensions of vacuum accumulator 101a are determined according to the volume of aerosol required for each application. According to some embodiments, to produce 30 mg of medical aerosol for local delivery to the lung or systematic delivery through the lung, a volume of at least 30 cc is required. Vacuum accumulator 101a has a path 101b through which the aerosol received from porous medium 102 enters vacuum accumulator 101a.

Nebulizer 100 further comprise a mouth-piece, also termed opening or exit hole 103, a structure opening 101d, cylinder piston 104, spring 105, cover 106 and duct 106b, according to some embodiments. Exit hole 103 is utilized for aerosol inhalation by a user when it is positioned against the structure opening 101d (see FIG. 2d). Exit hole 103 is blocked when it is positioned against an external wall of the outer structure 101 (see FIGS. 2a-2c). According to some embodiments, a vacuum or a low-pressure effect can be generated externally by a vacuum pump (e.g., for stationary use) or by an internal device included in the nebulizer itself. According to some embodiments, cylinder piston 104 is attached to spring 105, thereby displaced from one position wherein spring 105 is compressed (see FIGS. 2a-2b) to other positions, towards the bottom of outer structure 101, when spring 105 is released (see FIG. 2c). This movement of cylinder piston 104 results in a desired pressure drop, due to the vacuum or sub-atmospheric pressure generated in vacuum accumulator 101a, needed for aerosol production, according to some embodiments. The upper side of nebulizer 100 comprises a grove (not numbered) configured for placement of porous medium 102, according to some embodiments. Porous medium 102 is fixed or sealed to the device by cover 106, designed for fast opening/closing, according to some embodiments. Cover 106 has duct 106b extended between cover 106 and the external environment, according to some embodiments.

According to some embodiments, porous medium 102 may be located in any position within nebulizer 100. According to some embodiments, porous medium 102 is located at the upper side of nebulizer 100 (as shown in FIGS. 2a-2c) but can also be located on the opposite (bottom side) or in any side of nebulizer 100.

FIG. 2a shows nebulizer 100 prepared for generation of aerosol, in accordance with some embodiments. Fixture 108 includes notch 108a. The formation of notch 108a enables fixture 108 to be engaged with piston slot 104a in such a manner that piston 104 is maintained in a first optional compressed position. In this first optional position, spring 105 is compressed such that the distance between the lower edge of piston 104 and the bottom of vacuum accumulator 101a is H1. Porous medium 102 is fixed to nebulizer 100 by cover 106; and exit hole 103 is blocked by outer structure 101.

FIG. 2b shows nebulizer 100 prepared for generation of aerosol, in accordance with some embodiments. Notch 108a is engaged with piston slot 104b in such a manner that piston 104 is maintained in a second optional compressed position. In this second optional position, spring 105 is compressed such that the distance between the lower edge of piston 104 and the bottom of the vacuum accumulator 101a is H2.

It will be understood that piston 104 of nebulizer 100, prepared for generating aerosol, can be maintained either in first optional compressed position (see FIG. 2a) or in a second optional compressed position (see FIG. 2b), prior to the release of the spring 105.

In accordance with some embodiments, H1 and H2 are not equal. In accordance with some embodiments, H2 is longer than H1.

FIG. 2c shows nebulizer 100 in the instant right after the release of the fixture 108, also referred to as the stage of aerosol generation. Fixture 108 is designed as a lever, according to some embodiments, thereby configured to release notch 108a from either piston slot 104a or piston slot 104b, when pressure is applied to the bottom portion of fixture 108, i.e. the portion of fixture 108 opposite to the location of notch 108a. The displacement of notch 108a releases piston 104, thereby releasing spring 105 from its compressed state, either at first optional compressed position or at second optional compressed position, to a released position. In the released position, spring 105 displaces piston 104 towards the bottom of outer structure 101, thereby creating vacuum or sub-atmospheric pressure, in vacuum accumulator 101a. The pressure drop created across porous medium 102 generates aerosol within vacuum accumulator 101a.

While fixture 108 illustrated in FIGS. 2a-2d is designed as a lever, it will be understood that fixture 108 may be formed to accommodate other methods known in the art for release of notch 108a by a user.

Without wishing to be bound by any theory or mechanism of action, the magnitude of pressure drop across porous medium 102 is proportional to the initial distance between the lower edge of the piston 104 and the bottom of the vacuum accumulator 101a, such that if distance H2 is longer than H1, the pressure in aerosol accumulator 101a at the instant after spring 105 is released is lower in the case that piston 104 was positioned in the second optional compressed position, at height H2, compared to the case wherein piston 104 was positioned in the first optional compressed position, at height H1. Therefore, the former results in a higher pressure drop than the later. Thus, as there are more than one optional position for piston 104 prior to the release of spring 105 a range of different pressure drops can be generated. Thus, user of nebulizer 100 can choose pressure drops, based on the desired parameters of the resulting aerosol, such as, but not limited to: MMAD, GSD or aerosol concentration.

Figure 2D:
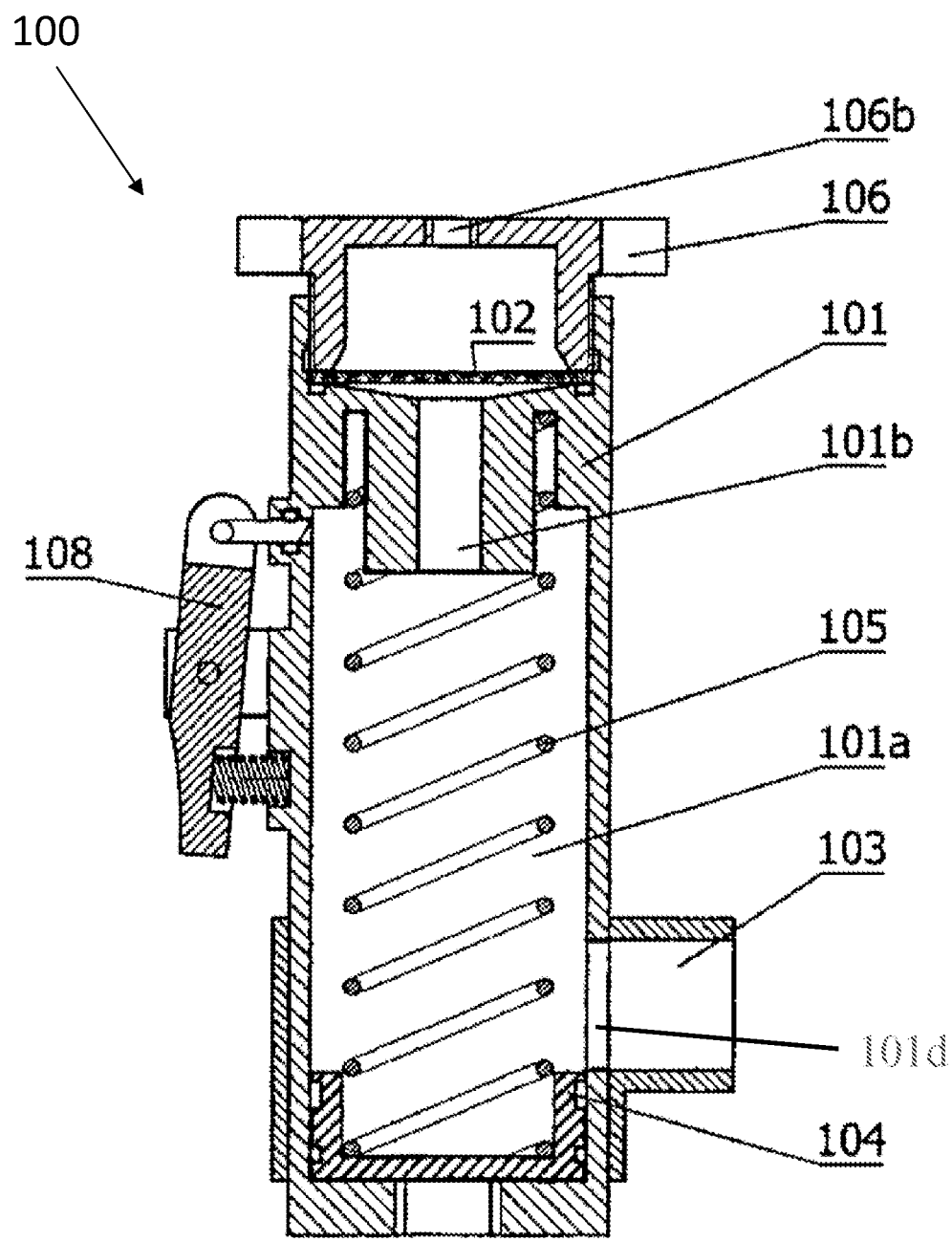

While FIGS. 2b-2c illustrate two piston slots 104a and 104b located at different levels, it will be understood that piston 104 may include any number of piston slots, thereby having any corresponding number of optional compressed positions, allowing an operator to choose between such positions in order to regulate the magnitude of the pressure drop across porous medium 102. FIG. 2d shows nebulizer 100 prepared for aerosol inhalation by a user: exit hole 103 is displaced to a position in front of structure opening 101d, thereby exposing the contents of aerosol accumulator 101a to the outside environment, allowing the aerosol to be nebulized by the user.

According to some embodiments, the aerosol within aerosol accumulator (or chamber, or vacuum accumulator 102a) is stored in low pressure or in vacuum, wherein positioning outlet 103 in front of structure opening 101d (see FIG. 2d), exposes vacuum accumulator 101a to the atmospheric pressure, rendering an equilibrium such that the pressure within vacuum accumulator 101a is atmospheric as well, prior to inhalation by the user.

According to some embodiments, duct 106b is kept open to the atmosphere. When low pressure is generated in aerosol accumulator 101a at the first instant after the release of spring 105 (which is allowing generation of aerosol) air enters nebulizer 100 through duct 106b, creating a new equilibrium of steady state in which the pressure within vacuum accumulator 101a is atmospheric pressure.

Figure 3:
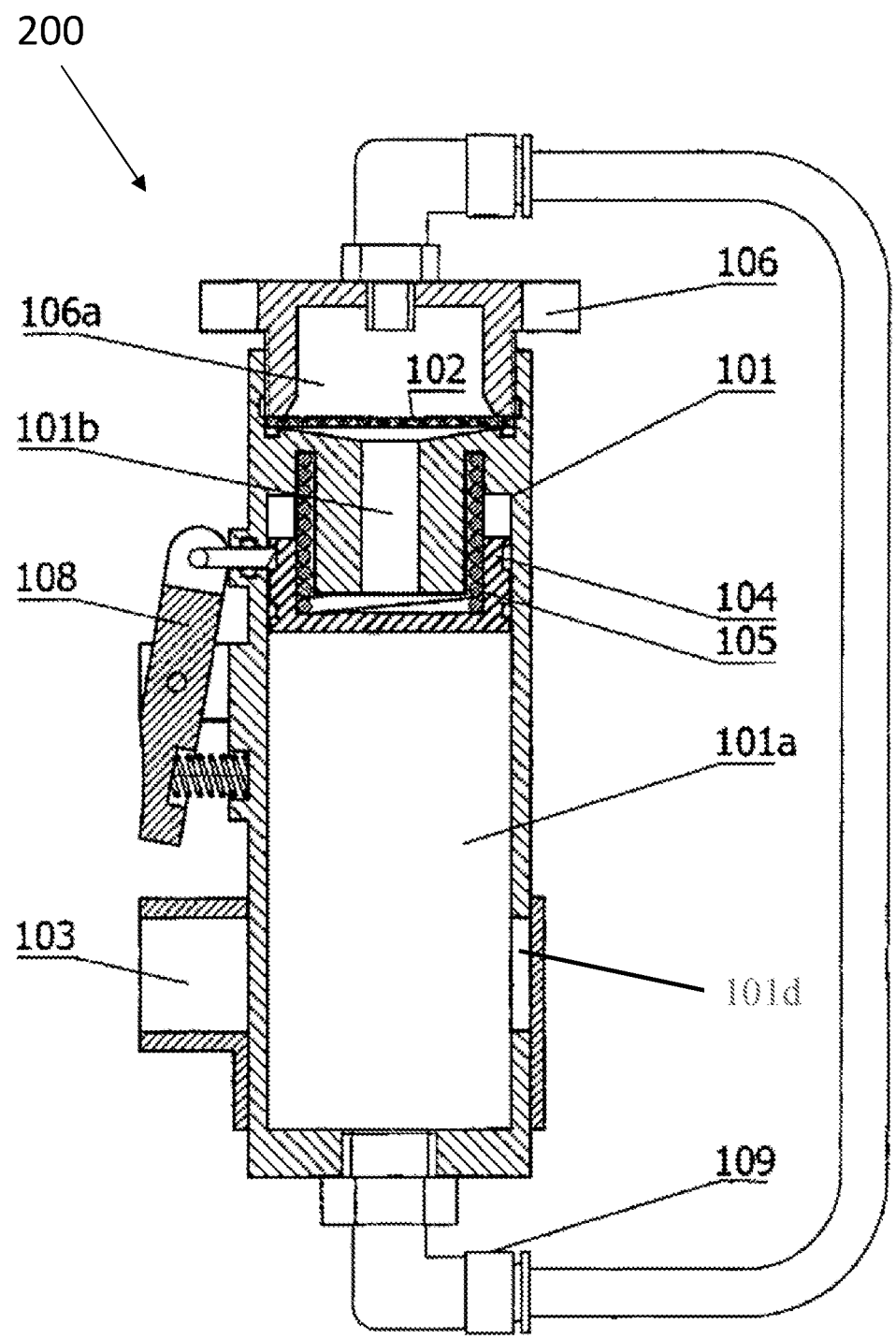

Reference is now made to FIG. 3, which schematically illustrates nebulizer 200 comprising porous medium 102. Nebulizer 200 is similar in function and structure to nebulizer 100, and further comprises tube 109. Tube 109 is used for supply of air during the aerosol generation stage. Tube 109 extends from vacuum accumulator 101a to duct 106b, and delivers gas in that direction to increase aerosol capacity by increasing dispersing gas.

Without being bound by any theory or mechanism, introducing additional dispersing gas increases the magnitude of the pressure drop across porous medium 102.

What is claimed is:

1. A nebulizer for producing aerosol, comprising:
   a porous medium, wherein the porous medium is rigid, has two flat sides and comprises:
      a plurality of pores; a liquid partially absorbed in the porous medium; and
      gas, wherein the gas is caged in pores that are vacant of said liquid, wherein the porous medium is configured to act as a pneumatic multi-nozzle atomizing system to release the aerosol; and
   means configured to create a pressure drop between the two flat sides of the porous medium, the means comprises a piston and a spring, wherein the spring is connected to the piston, and wherein the means are configured to generate at least two different magnitudes of said pressure drop;
   a fixture, wherein the piston comprises a plurality of piston slots, wherein the fixture is configured to adapt to any one of the plurality of piston slots, thereby compressing the spring at a plurality of heights.

2. The nebulizer of claim 1, wherein the diameter of the pores in the porous medium is below 1 micrometer.

3. The nebulizer of claim 1, wherein the overall contents of vacant space within the porous medium at least 10% liquid contents.

4. The nebulizer of claim 1, wherein the porous medium has a modulus of rigidity of at least 10 GPa at 25° C.

5. The nebulizer of claim 1, further comprising a chamber and a path, wherein the path is configured to receive the aerosol from the porous medium and transfer said aerosol to the chamber.

6. The nebulizer of claim 1, wherein the aerosol comprises droplets of the liquid, the droplets having a mass median aerodynamic diameter (MMAD) within the range of 0.3 to 7 micron.

7. The nebulizer of claim 6, wherein the MMAD of said droplets is in a range of 0.3 to 1.1 micrometer.

8. The nebulizer of claim 6, wherein the pressure drop is within a range of 600 to 900 mbar.

9. The nebulizer of claim 1, wherein the liquid comprises a pharmaceutical composition.

10. The nebulizer of claim 1, wherein the porous medium is disposable.

11. The nebulizer of claim 1, wherein the aerosol is ultra-fine highly concentrated aerosol comprising at least $10^9$-$10^{11}$ droplets per $cm^3$.

12. A method for treating a disease or disorder related to the respiratory system in a subject in need thereof, comprising, administering to the subject a pharmaceutical composition for treatment of said disease or disorder by inhalation, using the nebulizer of claim 1.

13. The method of claim 12, wherein the diameter of the pores of the porous medium is below 1 micrometer.

14. A method for producing aerosol, comprising the steps of:
   a) providing the nebulizer of claim 1; and
   b) generating a pressure drop across the porous medium, thereby obtaining aerosol.

15. The method of claim 14, wherein the pressure drop is within a range of 500 to 900 mbar.

16. The nebulizer of claim 1, wherein the rigidity of the rigid porous medium is not substantially effected upon being in contact with liquids.

17. The nebulizer of claim 1, wherein the porous medium comprises a metal.

18. The nebulizer of claim 1, wherein the porous medium is substantially devoid of materials having modulus of rigidity lower than 10 GPa 25° C.

19. The nebulizer of claim 1, wherein the nebulizer does not include an external gas supply in order to achieve aerosol formation.

20. The nebulizer of claim 1, further comprising a mouthpiece configured to deliver the aerosol to the lungs of a subject by inhalation.

21. The nebulizer of claim 20, further comprising an outer structure blocking the mouthpiece, the outer structure having a structure opening, wherein in the first position, the mouthpiece is positioned against a wall of the outer structure, and in the second opening the mouthpiece is displaced to a position in front of the structure allowing the aerosol to be nebulized and administered to the subject.

* * * * *